United States Patent
Hofer Kraner et al.

(10) Patent No.: US 10,926,348 B2
(45) Date of Patent: Feb. 23, 2021

(54) DETECTION DEVICE FOR AN ACTIVE GLARE PROTECTION DEVICE

(71) Applicant: Optrel Holding AG, Appenzell (CH)

(72) Inventors: Ramon Hofer Kraner, Herisau (CH); Tindaro Pittorino, Buchs/SG (CH); Olaf Schreiber, Buchs/SG (CH)

(73) Assignee: Optrel Holding AG, Appenzell (CH)

( * ) Notice: Subject to any disclaimer, the term of this patent is extended or adjusted under 35 U.S.C. 154(b) by 158 days.

(21) Appl. No.: 16/019,827

(22) Filed: Jun. 27, 2018

(65) Prior Publication Data
US 2019/0143437 A1 May 16, 2019

(30) Foreign Application Priority Data
Jun. 28, 2017 (EP) .................................... 17178387

(51) Int. Cl.
| | |
|---|---|
| *B23K 9/095* | (2006.01) |
| *H04L 29/08* | (2006.01) |
| *A61F 9/06* | (2006.01) |
| *B23K 9/32* | (2006.01) |
| *B23K 37/00* | (2006.01) |
| *G02F 1/133* | (2006.01) |
| *H04W 4/80* | (2018.01) |

(52) U.S. Cl.
CPC ............ *B23K 9/0956* (2013.01); *A61F 9/067* (2013.01); *B23K 9/322* (2013.01); *B23K 37/006* (2013.01); *G02F 1/13318* (2013.01); *H04L 67/12* (2013.01); *H04W 4/80* (2018.02)

(58) Field of Classification Search
CPC .... B23K 9/0956; B23K 9/322; B23K 37/006; G02F 1/13318; A61F 9/067
See application file for complete search history.

(56) References Cited

U.S. PATENT DOCUMENTS

| | | | | |
|---|---|---|---|---|
| 4,556,983 | A | * 12/1985 | Heitmann | ........ G11B 20/10009 |
| | | | | 327/166 |
| 2003/0061560 | A1 | * 3/2003 | Furukawa | .............. H03M 13/11 |
| | | | | 714/764 |
| 2005/0097648 | A1 | 5/2005 | Ackermann | |

(Continued)

FOREIGN PATENT DOCUMENTS

| | | |
|---|---|---|
| WO | 02/49554 A1 | 6/2002 |
| WO | 2015/200492 A1 | 12/2015 |

OTHER PUBLICATIONS

European Search Report dated Nov. 13, 2017 for the corresponding EP application No. 17178387.1(English translation attached).

(Continued)

*Primary Examiner* — Ibrahime A Abraham
*Assistant Examiner* — John J Norton
(74) *Attorney, Agent, or Firm* — Posz Law Group, PLC

(57) ABSTRACT

A detection device for an active glare protection device comprises a detection unit that is configured for a direct or indirect detection of at least one welding parameter of a welding apparatus, and comprises at least one communication unit that is configured for a transmission of at least one information of the at least one welding parameter to the active glare protection device, wherein the communication unit is configured for a transmission of at least one information of the at least one welding parameter, implemented as a bit sequence of a defined length, to the active glare protection device.

14 Claims, 4 Drawing Sheets

(56) References Cited

U.S. PATENT DOCUMENTS

Figure 1:
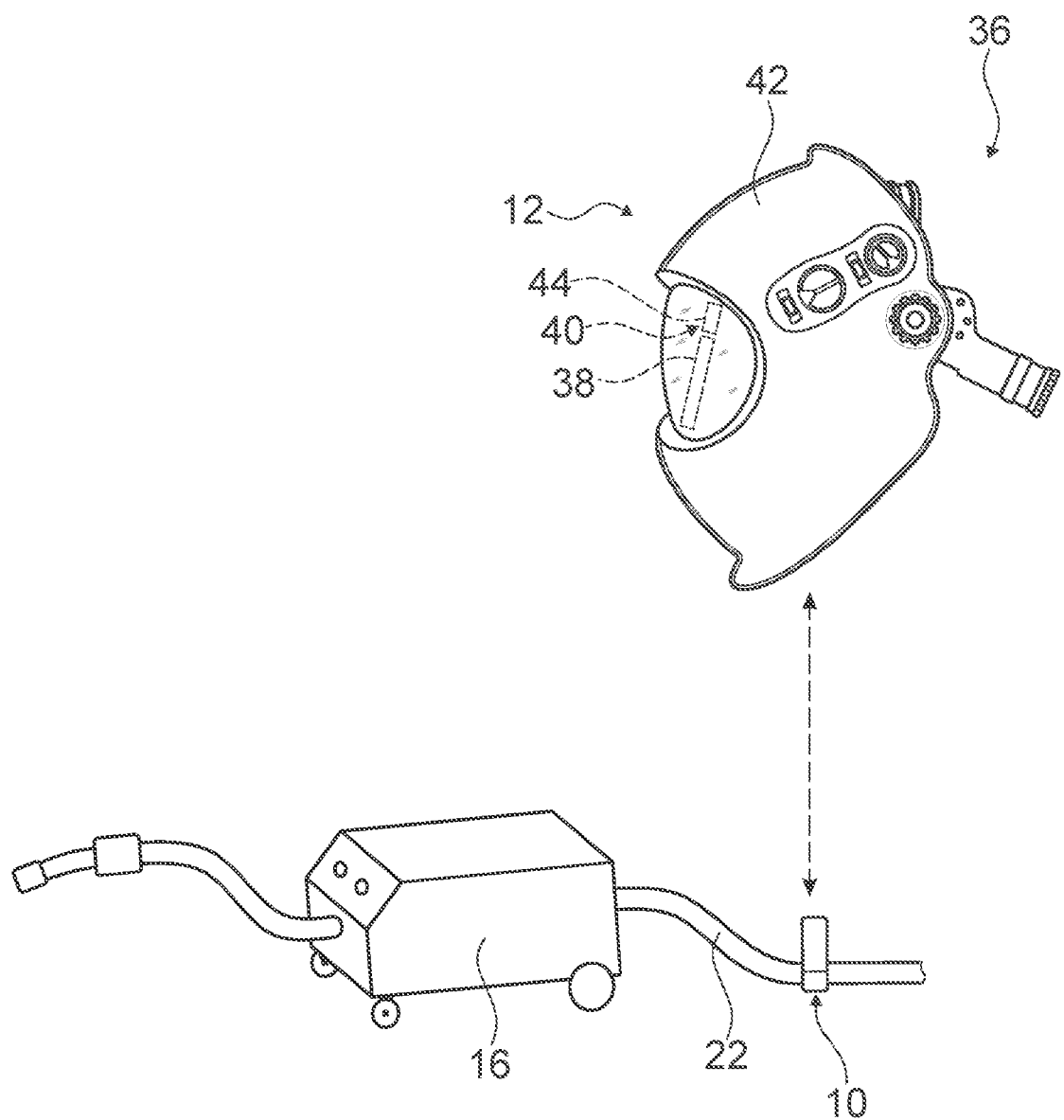

| | | |
|---|---|---|
| 2007/0221636 A1 | 9/2007 | Monzyk |
| 2014/0183176 A1* | 7/2014 | Hutchison .............. B23K 9/322 |
| | | 219/124.02 |
| 2014/0320771 A1 | 10/2014 | Keller et al. |
| 2016/0292557 A1* | 10/2016 | Kolman ............. G06K 19/0724 |

OTHER PUBLICATIONS

Block code—Jun. 20, 2017, Wikipedia, https://en. wikipedia.org/w/index. php?title= Block_ code&oldid=786615062.

* cited by examiner

DETECTION DEVICE FOR AN ACTIVE GLARE PROTECTION DEVICE

CROSS REFERENCE TO RELATED APPLICATION

This application is based on and incorporates herein by reference European Patent Application No. 17178387.1 filed on Jun. 28, 2017.

STATE OF THE ART

The invention relates to a detection device for an active glare protection device.

A detection device for an active glare protection device, with a detection unit that is configured for a direct or indirect detection of at least one welding parameter of a welding apparatus, and with at least one communication unit that is configured for a transmission of at least one information of the at least one welding parameter to the active glare protection device, has already been proposed.

The objective of the invention is in particular to provide a generic device with improved characteristics regarding a transmission speed as well as a transmission reliability, in particular of the communication unit. The objective is achieved, according to the invention, by the features of the independent claim while advantageous implementations and further developments of the invention may be gathered from the dependent claims.

Advantages of the Invention

The invention is based on a detection device for an active glare protection device, with a detection unit that is configured for a direct or indirect detection of at least one welding parameter of a welding apparatus, and with at least one communication unit that is configured for a transmission of at least one information of the at least one welding parameter to the active glare protection device.

It is proposed that the communication unit is configured for a transmission of at least one information of the at least one welding parameter, implemented as a bit sequence of a defined length, to the active glare protection device. This allows in particular achieving an advantageously high transmission speed as well as an advantageously high transmission reliability. Due to the transmission as a bit sequence of a defined length, it is in particular possible to dispense with additional information, e.g. CRC and Syncword, which are necessary for a package-oriented transmission. It is thus possible to realize the transmission package in a substantially shorter implementation. This allows achieving an advantageously fast data transmission. Moreover an advantageously high robustness of a transmission channel is achievable as the information, in particular signal states, is/are transmitted not just as single bits but by bit sequences of a defined length. Such an implementation allows keeping a potential influence of interference signals low by means of signal processing. While a transmission time of a signal state is correspondingly lengthened by this, it is still shorter than in a package-oriented transmission. The latency periods are determined by the number of bits for a realization of a signal state and by the modulation rate. A maximum switch time from one signal state to another one is twice the transmission time of a bit sequence. This is due to the independency of switch process and radio transmission. The two processes do not work synchronously. Herein the times required for signal processing are not taken into account. Signal transit times in a wireless interface are negligible in case of low-distance applications. In this way it is therefore in particular possible to achieve the shortest possible latency periods in a data transmission of the information, in particular of at least two signal states, like for example for a quick darkening of a welding helmet.

An "active glare protection device" is in particular to mean, in this context, a glare protection device with an active optical glare protection filter. By a "glare protection device" is in particular, in this context, a device to be understood which is configured for a protection of a user from excess brightness and/or from sparks. Preferentially it is in particular to mean a device serving for a protection of a user's eyes and/or of a user's facial region during a welding and/or grinding process. Preferably it is in particular to be understood as a glare protection device which in particular serves for a protection of the user's eyes at least during a welding process. Different implementations of a glare protection device, deemed expedient by someone skilled in the art, are conceivable, like for example as a welding helmet, as a welding screen, as a welding mask and/or as a welding shield. Furthermore, an "active optical glare protection filter" is herein in particular to be understood as an optical filter, which in particular implements a protective glass and/or a protective synthetic glass. It is preferably to mean in particular an optical filter the light permeability of which is implemented to be adjustable. It is preferentially in particular to mean an optical welding protection filter with an automatic darkening. Especially preferentially the glare protection filter comprises at least one liquid-crystal plane which is switchable in the transmittance. A variety of implementations of the optical glare protection filter are conceivable which are deemed expedient by someone skilled in the art, and an optical glare protection filter is in particular to mean an ADF, also called an "automatic darkening filter" or an "automatic welder's protection filter". Furthermore, a "detection unit" is in particular, in this context, to mean a unit which is configured for a direct or indirect detection of at least one welding parameter of a welding device. Herein the detection unit may in particular be configured for a direct detection of the welding parameter and may also be configured to deduce the at least one parameter by a detection of alternative characteristics. The detection unit preferably comprises at least one sensor. Herein a "sensor" is in particular to mean, in this context, an element that is configured to detect at least one parameter and/or physical property, wherein the detection may take place in an active manner, like in particular by generating and emitting an electrical measuring signal, or in a passive manner, like in particular by capturing property changes of a sensor component. Different sensors deemed expedient by someone skilled in the art are conceivable. "Configured" is in particular to mean specifically programmed, designed and/or equipped. By an object being configured for a certain function is in particular to be understood that the object fulfills and/or implements said certain function in at least one application state and/or operation state. A "welding parameter of the welding apparatus" is furthermore in particular to mean, in this context, a parameter of an operation of the welding apparatus. It is preferentially in particular to mean a parameter allowing deductions regarding an operation state, in particular a status, of the welding apparatus. Different welding parameters deemed expedient by someone skilled in the art are conceivable, like for example a welding current.

By a "communication unit" is in particular, in this context, a unit to be understood which is configured to provide a communication, in particular a wireless communication, with the active glare protection device. For a communication with the active glare protection device, the communication unit preferentially comprises at least one interface. Preferably a "communication unit" is in particular to mean a unit which is configured for an exchange of data. In particular the communication unit comprises at least one information entry and at least one information exit. Preferentially the communication unit comprises at least two information entries and at least two information exits, wherein at least one information entry and at least one information exit are respectively configured for a connection to a physical system, in particular the external welding apparatus. Especially preferentially a communication unit is to be understood as an interface between at least two physical systems, like in particular between the active glare protection device and the detection device. While different communication units, deemed expedient by someone skilled in the art, are conceivable, a communication unit is in particular to be understood as a wireless interface, like for example Bluetooth, WLAN, Zigbee, NFC, RFID, GSM, LTE or UMTS, and/or as a wire-bound interface, like for example a USB terminal, a CAN bus interface, an RS485 interface, an Ethernet interface, an optical interface, a KNX interface and/or a Powerline interface. By a "bit sequence of a defined length" is in particular, in this context, a sequence of at least two bits to be understood, wherein the sequence always has the same number of bits for each transmitted information. The information is therefore preferably always transmitted by means of a sequence with the same number of bits. The bit sequence herein has the same number of bits in particular independently from the information contained.

It is also proposed that the communication unit is configured for a wireless transmission, in particular by means of a radio connection, of the at least one information of the at least one welding parameter, implemented as a bit sequence of a defined length, to the active glare protection device. This in particular allows achieving an advantageously comfortable transmission of the information. It is in particular possible to dispense with an encumbering cable.

Furthermore it is proposed that the communication unit comprises at least one transmission unit that is configured for a direct transmission of a signal to the active glare protection device, and comprises at least one modulation unit, which is configured for a modulation of the at least one welding parameter, implemented as a bit sequence of defined length, directly onto the signal. The transmission unit is preferably configured to generate a carrier signal which the bit sequence of defined length can be modulated onto. Preferably in particular a proprietary radio signal is used for this. A communication is moreover in particular realized in a uni-directional manner, wherein the information transmission is effected via the transmission unit in a streaming process. This in particular allows achieving an advantageously fast data transmission. It is in particular possible to use a direct modulation, which allows at least substantially dispensing with time-consuming data processing. It is therefore in particular possible to use an unbuffered data transmission, i.e. a direct modulation, respectively demodulation, without involving a package handler. By a "transmission unit" is in particular, in this context, a unit to be understood which is configured to generate a signal, in particular a carrier signal. The transmission unit is preferably embodied by a radio transmission unit, which is configured to generate a radio signal. The transmission unit in particular implements a radio interface. Beyond this, a "modulation unit" is in particular to mean, in this context, a unit which is configured for a modulation of a signal of the transmission unit. It is preferentially to be understood as a unit configured for a modulation of data and/or information, implemented as bits, onto a signal of the transmission unit. The modulation is herein achievable, for example, by a frequency modulation. Different modulation units, deemed expedient by someone skilled in the art, are conceivable, e.g. an HF transceiver component with a direct modulation. Components permitting a package-oriented transmission only are preferably not suitable. However, a synchronous modulation and/or demodulation are/is not a necessity.

Beyond this it is proposed that the at least one transmission unit is configured for a proprietary, non-packaged transmission of the signal to the active glare protection device. In this way in particular an advantageously high transmission speed as well as an advantageously high level of transmission reliability are achievable. The non-packaged transmission in particular allows dispensing with additional information, e.g. CRC and Syncword, which is required in a package-oriented transmission. A transmission package may therefore be implemented in a substantially shorter fashion. This allows achieving an advantageously fast data transmission. By a "non-packaged transmission" is in particular, in this context, a transmission to be understood in which a transmission is effected in a non-packaged manner. A transmission is thus not effected in a package-oriented manner, which means no CRCs and/or Syncwords are used.

It is further proposed that the at least one communication unit is configured for a uni-directional transmission of at least one information of the at least one welding parameter to the active glare protection device. Preferentially the transmission of the at least one information of the at least one welding parameter to the active glare protection device is effected in a streaming procedure. In this way in particular an advantageously safe and reliable transmission is achievable. It is possible to avoid delays in the signal transmission. It is preferably possible that a signal is transferred to the active glare protection device in a continuous manner.

Moreover it is proposed that a bit sequence of the communication unit comprises at least 4 bits, preferably at least 6 bits. A bit sequence of the communication unit preferentially comprises less than 32 bits, especially preferentially less than 16 bits. Preferably a bit sequence of the communication unit comprises exactly 8 bits. Principally however another number of bits, deemed expedient by someone skilled in the art, is also conceivable. In this way it is possible to ensure an advantageously safe transmission. This also allows an unambiguous reconstruction of a valid signal even in an interference-affected environment. A robustness of the data transmission increases with increasing length of the bit sequence. However, this affects the achievable minimum latency periods. The bit sequence may in particular be adapted to a respective application case.

It is also proposed that the at least one modulation unit is configured for a modulation of the signal of the at least one transmission unit with a modulation rate of at least 100 kbit/s, preferably at least 400 kbit/s and particularly preferably at least 800 kbit/s. This in particular allows achieving an advantageously fast data transmission. In particular, an advantageously high transmission speed as well as an advantageously high level of transmission reliability are achievable.

It is further proposed that, for a direct modulation of the signal of the at least one transmission unit, the at least one modulation unit comprises at least one HF transceiver component. The HF transceiver component is preferentially implemented by a direct-modulation HF transceiver component. In this way an advantageous modulation unit may be rendered available.

Furthermore it is proposed that the detection unit is configured for a direct or indirect detection of at least two switch states of the welding apparatus. Preferably the detection unit is configured for a direct or indirect detection of at least one welding operation state and at least one rest state, in particular the states "welding inactive" and "welding active", of the welding apparatus. This allows achieving an advantageous detection. In particular for an early darkening of the active glare protection filter, it is in this way possible to detect a state of the welding apparatus reliably, and in particular independently from the welding apparatus.

It is also proposed that the at least one communication unit is configured for a direct transmission of the two switch states of the welding apparatus, implemented as mutually inverse bit sequences, to the active glare protection device. Preferably respectively one bit sequence is allocated to each switch state, wherein the bit sequences are respectively inverse to one another, which means that each bit of the bit sequence has the respectively opposite value. This allows unambiguously allocating each bit sequence, even in case of a noise-affected environment and non-readable bits. This representation makes it possible to keep a possible impact of interference signals low by means of a signal processing. A transmission time of a signal state is thus correspondingly increased but is still shorter than in a package-oriented transmission.

The invention is furthermore based on a system with the active glare protection device and with the detection device.

The invention is also based on a method for an operation of the detection device.

Herein the detection device according to the invention, the system and the method are not to be limited to the application and implementation form described above. In particular, to fulfill a functionality that is described here, the detection device according to the invention, the system and the method may comprise a number of respective elements, components and units that differs from a number that is mentioned here.

DRAWINGS

Further advantages will become apparent from the following description of the drawings. In the drawings an exemplary embodiment of the invention is shown. The drawings, the description and the claims contain a plurality of features in combination. Someone skilled in the art will purposefully also consider the features individually and will find further expedient combinations.

Figure 2:
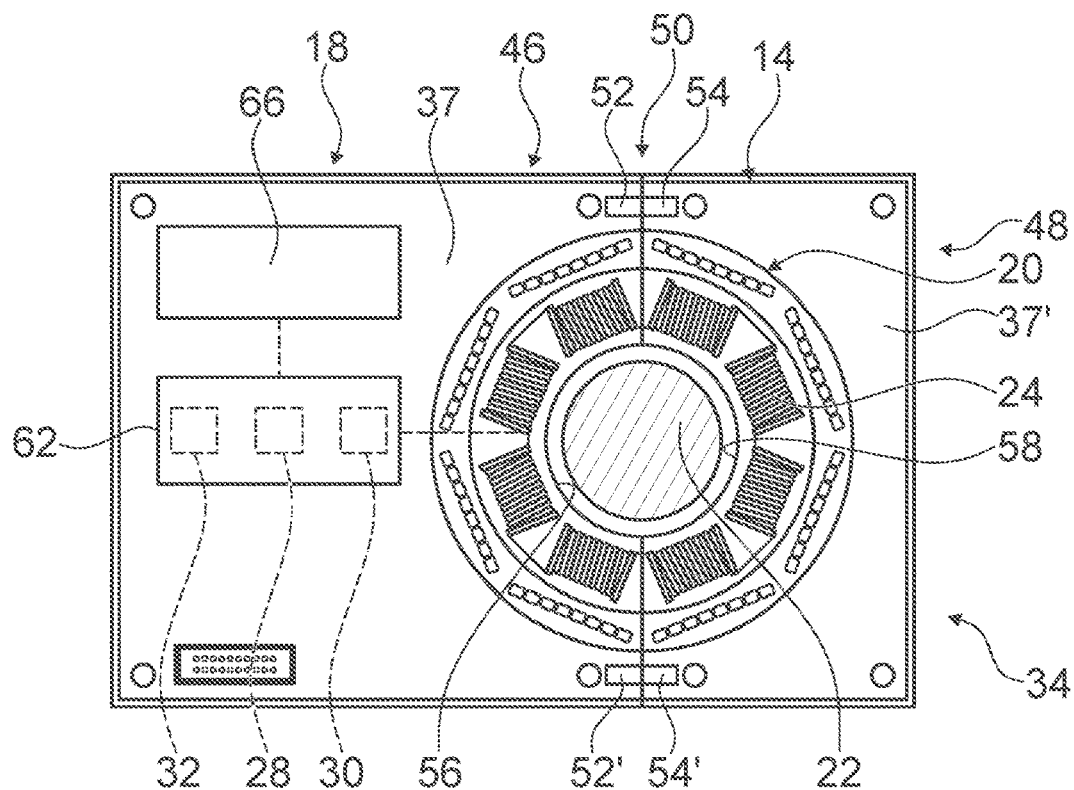
Figure 3:
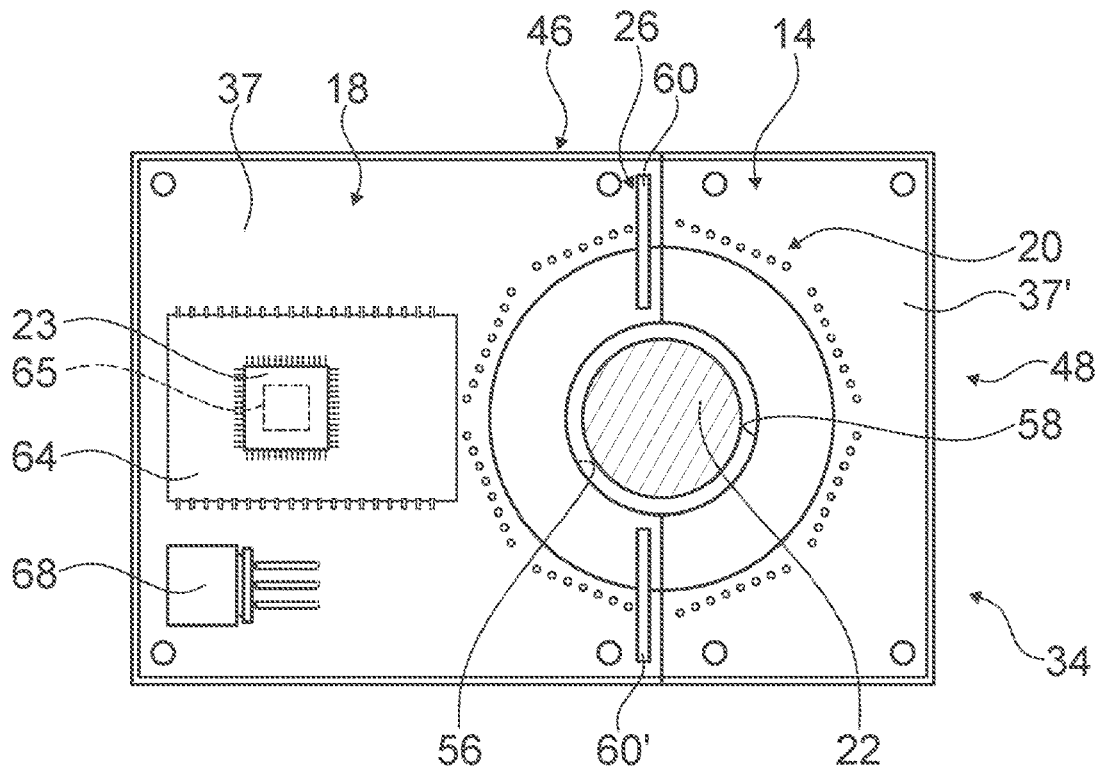
Figure 4:
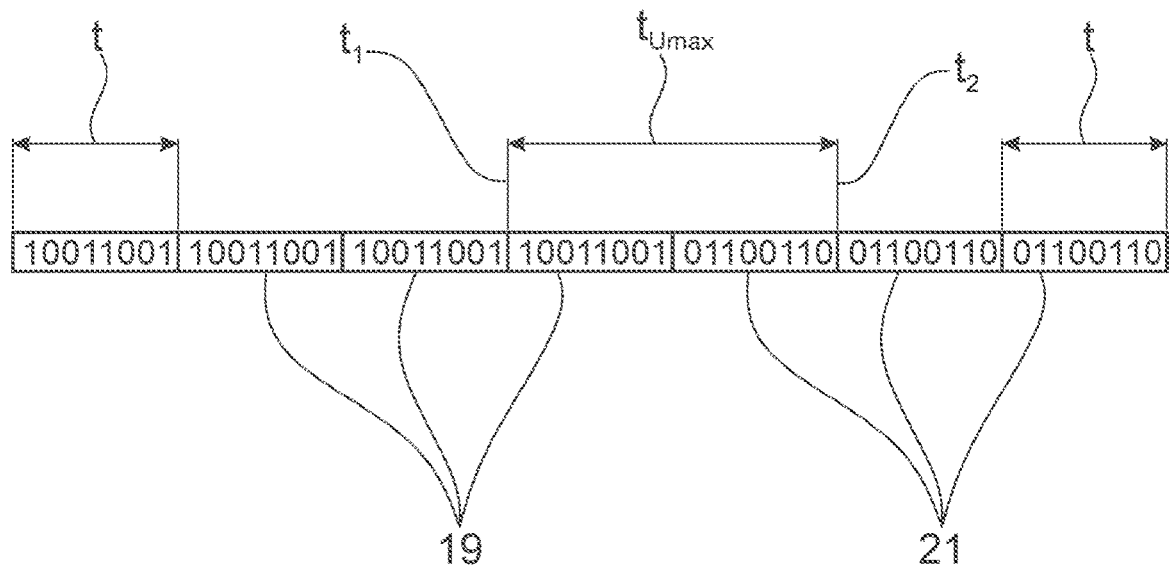
Figure 5:
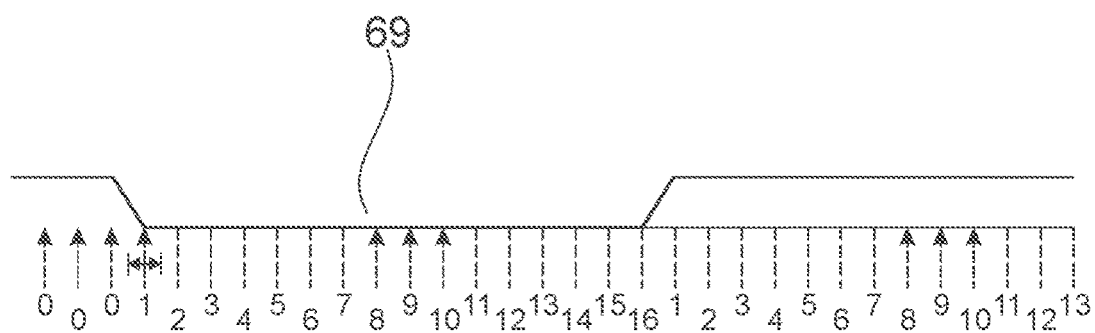
Figure 6:
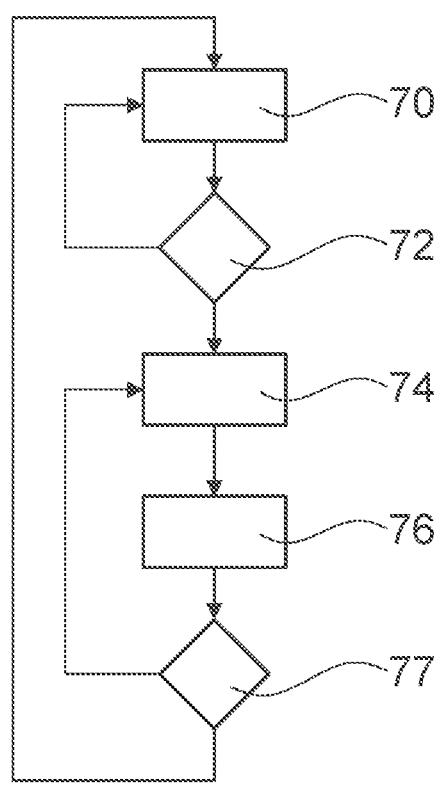

It is shown in:

FIG. 1 a system with an active glare protection device and with a detection device according to the invention, as well as a welding apparatus, in a schematic representation, FIG. 2 the detection device according to the invention with a detection unit and with a communication unit, in a schematic front view, FIG. 3 the detection device according to the invention with the detection unit and with the communication unit, in a schematic rear view, FIG. 4 an illustration of a package structure of the communication unit of the detection device according to the invention, in a schematic representation, FIG. 5 an illustration of a data scanning of a signal of the communication unit of the detection device according to the invention by a communication unit of the active glare protection device, in a schematic representation, and FIG. 6 a schematic flow chart of a method for an operation of the detection device according to the invention.

DESCRIPTION OF THE EXEMPLARY EMBODIMENT

FIG. 1 shows an active glare protection device 12, a detection device 10 and a welding apparatus 16. The welding apparatus 16a is embodied by an arc welding apparatus. Principally however a different implementation of the welding apparatus 16, deemed expedient by someone skilled in the art, would also be conceivable.

The glare protection device 12 and the detection device 10 implement a system 36. The glare protection device 12 is configured to be worn by a user on his head during operation. The glare protection device 12 is embodied by a welding helmet. Principally however a different implementation of the glare protection device 12, deemed expedient by someone skilled in the art, would also be conceivable. The detection device 10 is implemented separately from the glare protection device 12.

The glare protection device 12 comprises an optical glare protection filter 38. The glare protection filter 38 is configured to change a permeability depending on an operative state and on an actuation that depends on the operative state. The optical glare protection filter 38 is implemented by an electro-optical filter. The optical glare protection filter 38 is implemented by an automatic darkening filter, short ADF. The optical glare protection filter 38 consists of a plurality of layers. The optical glare protection filter 38 is implemented as a multi-layer-compound. During operation a liquid-crystal layer of the optical glare protection filter 38 is darkened by a computing unit 40 if a welding process is detected. The optical glare protection filter 38 has a rectangular basic shape.

The glare protection device 12 further comprises a shield unit 42. The glare protection filter 38 is fixedly accommodated in the shield unit 42. The glare protection filter 38 is accommodated in the shield unit 42 fixedly in regard to a position. The glare protection device 12 moreover comprises a front cover plate. The front cover plate is connected to the shield unit 42 via latch elements, which are not shown in detail. The front cover plate is embodied transparent. The front cover plate is configured for a protection of the glare protection filter 38. The front cover plate covers the glare protection filter 38 from an outside.

Furthermore the glare protection device 12 comprises a communication unit 44. The communication unit 44 is configured for a communication with the detection device 10, which is separate from the glare protection 12. The communication unit 44 is configured to receive signals from the detection device 10, which is separate from the glare protection device 12. The communication unit 44 is integrated in the computing unit 40. The communication unit 44 implements a portion of the computing unit 40. Principally however a separate implementation of the communication unit 44 would also be conceivable. Via the communication unit 44, the glare protection device 12 is capable of receiving signals for a darkening of the glare protection filter 38. Via the communication unit 44, the glare protection device 12 is capable of receiving welding parameters A of the welding apparatus 16, which have been detected by the detection device 10. The welding parameters A of the welding apparatus 16 are transmitted to the glare protection device 12 by the detection device 10. The computing unit 40 of the glare protection device 12 is configured for an evaluation of the welding parameters A of the welding apparatus 16. The computing unit 40 is further configured for a darkening of the glare protection filter 38, depending on the welding parameters A of the welding apparatus 16. It would herein in particular be conceivable that the computing unit 40 automatically darkens the glare protection filter 38 in case of an absence of a signal from the detection device 10. In this way, in case of an absence of a signal from the detection device 10, e-g. due to a too large distance between the glare protection device 12 and the detection device 10, a damage to a user could be excluded. Additionally or alternatively it would however also be conceivable that the computing unit 40 comprises an additional, in particular optical, sensor for a detection of an arc of the welding apparatus 16, via which a darkening of the glare protection filter 38 would also be possible.

The detection device 10 is configured for the active glare protection device 12. The detection device 10 implements an add-on component for the glare protection device 12. The detection device 10 and the glare protection device 12 are intended to be used together. The detection device 10 comprises a detection unit 14. The detection unit 14 is configured for a direct or indirect detection of at least one welding parameter A of the welding apparatus 16. The detection unit 14 is configured for an indirect detection of a current of the welding apparatus 16. The detection unit 14 is configured for a detection of a current flowing to the welding apparatus 16. The detection unit 14 is configured for an indirect detection of two switch states of the welding apparatus 16. The welding apparatus 16 has two switch states. The welding apparatus 16 has a welding operative state, which is in particular implemented by "welding active", and a rest state, which is in particular implemented by "welding inactive". The detection unit 14 is configured for an indirect detection of the welding operative state and of the rest state of the welding apparatus 16. The detection unit 14 deduces, via the welding parameter A, a switch state which the welding apparatus 16 is in. The detection unit 14 comprises a current sensor 20. The current sensor 20 is configured for a detection of the welding parameter A of the welding apparatus 16. The current sensor 20 is configured for a detection of a welding parameter A of the welding apparatus 16 which is realized by a current. For a detection of the welding parameter A of the welding apparatus 16, the current sensor 20 is configured to be fixated to a power cable 22 of the welding apparatus 16 in a variable fashion. The power cable 22 of the welding apparatus 16 is embodied by a torch cable and/or earth cable. For a detection of the at least one welding parameter A of the welding apparatus 16, the current sensor 20 is configured to be fixated to the power cable 22 of the welding apparatus 16 in an electrically contact-free, variable manner. The current sensor 20 is during operation fixated to a power cable 22 of the welding apparatus 16 in a variable manner. The entire detection device 10 is during operation fixated to a power cable 22 of the welding apparatus 16 in a variable manner. For this purpose, the detection device 10 engages around the power cable 22 of the welding apparatus 16. The detection device 10 is for this purpose fixated around the power cable 22 of the welding apparatus 16. The detection device 10 implements a clamp. The detection device 10 is fixatable in any position on the power cable 22 of the welding apparatus 16 and on any welding apparatus 16. The detection device 10 is capable of functioning independently from a welding apparatus 16 and is in particular capable of being fixated to welding apparatuses 16 of different manufacturers (FIGS. 1, 5).

The detection device 10 comprises a multi-part housing 34. The detection device 10 comprises a two-part housing 34. The housing 34 accommodates the detection unit 14 of the detection device 10. The housing 34 is configured to be assembled, without tools, around the power cable 22 of the welding apparatus 16. The housing 34 comprises a first half-housing 46 and a second half-housing 48. The half-housings 46, 48 respectively comprise, on sides facing each other, a recess 56, 58 for the power cable 22. The recesses 56, 58 of the half-housings 46, 48 are respectively embodied in a half-circle shape. The recesses 56, 58 together form a circle-shaped recess. The half-housings 46, 48 are connectable to one another via a connection unit 50. The connection unit 50 comprises two first connection elements 52, 52', which are fixedly connected with the first half-housing 46, and two second connection elements 54, 54', which are fixedly connected with the second half-housing 48. For a connection of the half-housings 46, 48, the first and second connection elements 52, 52', 54, 54' are screwed with one another. Principally however a different connecting technique, deemed expedient by someone skilled in the art, would also be conceivable like, for example, magnetically. It is thus possible, for an assembly, to separate the half-housings 46, 48 of the detection device 10 and then to close them again around the power cable 22 (FIGS. 2, 3).

Moreover the detection device 10 comprises a multi-part pcb (printed circuit board) 35. The pcb 35 is embodied in a two-part implementation. The pcb 35 comprises two separate pcb elements 37, 37'. The pcb elements 37, 37' are implemented correspondingly to the half-housings 46, 48. The first pcb element 37 is arranged in the first half-housing 46. The second pcb element 37' is arranged in the second half-housing 48. The pcb elements 37, 37' are configured to be mounted around the power cable 22 of the welding apparatus 16. For this, the pcb elements 37, 37' comprise recesses corresponding to the recesses 56, 58 of the half-housings 46, 48.

The current sensor 20 of the detection unit 14 further comprises a first sensor element 24. The first sensor element 24 is configured for a detection of a current change in the power cable 22 of the welding apparatus 16. In an operation, the first sensor element 24 engages around the power cable 22 of the welding apparatus 16. The first sensor element 24 of the current sensor 20 is arranged around the recesses 56, 58 of the half-housings 46, 48. The first sensor element 24 is embodied by a Rogowski coil. The first sensor element 24 is embodied by a Rogowski coil, which in an operation extends around the power cable 22 in a ring-shape. Preferably the Rogowski coil is composed of a plurality of partial coils. The first sensor element 24 is applied partially on the first pcb element 37 and partially on the second pcb element 37'. The first sensor element 24 is implemented of a plurality of air-core coils, which the pcb elements 37, 37' are loaded with. The first sensor element 24 is implemented of a plurality of SMD-loadable air-core coils (FIGS. 2, 3).

Furthermore the current sensor 20 of the detection unit 14 comprises a second sensor element 26. The second sensor element 26 is configured for a detection of an absolute current value in the power cable 22 of the welding apparatus 16. By means of the second sensor element 26 therefore in particular a continuous current value is also measurable. The second sensor element 26 comprises two measuring elements 60, 60', which are arranged on opposite sides of the recesses 56, 58 of the half-housings 46, 48. During operation the measuring elements 60, 60' are arranged on opposite sides of the power cable 22. The second sensor element 26 is embodied by a Hall sensor. The measuring elements 60, 60' of the second sensor element 26 are each embodied by Hall sensor boards (FIG. 3).

The detection device 10 also comprises a communication unit 18. The communication unit 18 is configured for a transmission of at least one information of the welding parameter A to the active glare protection device 12. The communication unit 18 of the detection device 10 is configured for a communication with the communication unit 44 of the glare protection device 12. The communication unit 18 of the detection device 10 is configured for a transmission of an information that results from the welding parameter A to the communication unit 44 of the glare protection device 12. The communication unit 18 of the detection device 10 is configured for a transmission of the actual switch state of the welding apparatus 16 to the communication unit 44 of the glare protection device 12. The communication unit 18 is configured for a transmission of the information of the welding parameter A, in particular the switch state, implemented as a bit sequence 19, 21 of a defined length, to the active glare protection device 12. The communication unit 18 is configured for a wireless transmission of the information of the welding parameter A, in particular the switch state, implemented as a bit sequence 19, 21 of a defined length, to the active glare protection device 12. The communication unit 18 is configured for a uni-directional transmission of the information of the at least one welding parameter A, in particular the switch state, to the active glare protection device 12. Herein a fix bit sequence 19, 21 is allocated to each of the two switch states of the welding apparatus 16. The bit sequences 19, 21 have the same number of bits. The bit sequences 19, 21 each have more than one bit. The communication unit 18 is configured to transmit the two switch states of the welding apparatus 16, which are implemented as mutually inverse bit sequences 19, 21, directly to the active glare protection device 12. The bit sequences 19, 21 are respectively inverse, and therefore each bit of the one bit sequence 19, 21 has the opposite value of the bit of the other bit sequence 19, 21 in the same position. The bit sequences 19, 21 of the communication unit 18 respectively comprise at least 4 bits. The bit sequences 19, 21 of the communication unit 18 respectively comprise precisely 8 bits. Principally another number of bits, deemed expedient by someone skilled in the art, would also be conceivable. The number of bits in particular realizes an advantageous relation of robustness and transmission speed. The robustness of the data transmission increases with an increasing length of the bit sequence 19, 21. However, this affects the achievable minimum latency times. The bit sequence is therefore adaptable to the respective application case.

The communication unit 18 comprises a signal processing unit 62. The signal processing unit 62 is implemented by an analogous signal processing. The signal processing unit 62 is configured for a processing of the data of the detection unit 14. The signal processing unit 62 is configured for a processing of the data of the detection unit 14 before a transmission. The signal processing unit 62 is coupled directly with the detection unit 14. The signal processing unit 62 comprises a differential amplifier 28, a rectifier 30 and a comparator 32. Furthermore the communication unit 18 comprises a transmission unit 64. The transmission unit 64 is embodied by a radio module. The transmission unit 64 is embodied by an RF module. The transmission unit 64 is implemented by a system-on-a-chip RF module, short: RF-SoC module. The transmission unit 64 is configured for a direct transmission of a signal to the active glare protection device 12. The transmission unit 64 is configured for a direct transmission of a radio signal to the active glare protection device 12. The transmission unit 64 is configured for a proprietary, non-packaged transmission of the signal to the active glare protection device 12.

The communication unit 18 also comprises a modulation unit 23. The modulation unit 23 is configured to directly modulate the at least one welding parameter A, implemented as a bit sequence 19, 21 of a defined length, directly onto the signal of the transmission unit 64. The modulation unit 23 is configured for a modulation of the signal of the one transmission unit 64 with a modulation rate of at least 100 kbit/s. The modulation unit 23 is configured for a modulation of the signal of the one transmission unit 64 with a modulation rate of approximately 1 Mbit/s. For a direct modulation of the signal of the transmission unit 64, the modulation unit 23 comprises an HF transceiver component 65. The modulation unit 23 comprises an HF transceiver component 65 with a direct modulation and/or demodulation. However, a synchronous modulation and/or demodulation are/is not a necessity. For a simple implementation of the streaming procedure of the communication unit 18, a standard UART, i.e. a Universal Asynchronous Receiver Transmitter, of a micro controller of the signal processing unit 62 of the communication unit 18 may be used as an HF transceiver component 65. The transmission signal is generated by a repeated transmission of the defined bit sequence 19, 21. When switching into the other switch state, the inverted bit sequence 19, 21 is transmitted. The output signal of the UART serves for a direct modulation of the transmission unit 64. A timing behavior is limited by the standardized data structure of the UART. Corresponding to the data protocol, there must be at least a start bit 69 and a stop bit. A transmission duration is accordingly increased.

FIG. 4 shows an illustrated package structure of the communication unit 18 of the detection device 10. The information is herein transmitted being implemented as the bit sequences 19, 21, wherein each bit sequence 19, 21 represents an information. Due to the defined number of bits of the bit sequences 19, 21 and to the defined modulation rate, the bit sequences 19, 21 respectively have a defined transmission time t. In the present exemplary embodiment the transmission time t is 8 μs. Therefore the maximum switch time $t_{Umax}$ from one signal state to the other one is therefore twice the transmission time t of a bit sequence 19, 21. For example, if at a point in time $t_1$, at the beginning of a transmission of a bit sequence 19, the welding apparatus 16 is switched from the welding operating state, which is represented by the communication unit 18 via the first bit sequence 19, into the rest state, which is represented by the communication unit 18 via the second bit sequence 21, it is possible to transmit the second bit sequence 21 only when the transmission of the first bit sequence 19 is finished. The second bit sequence 21 must be completely transmitted before the information that the welding apparatus 16 is in a rest state is detected by the communication unit 44 of the glare protection device 12 at a point in time $t_2$. The maximum switch time $t_{Umax}$ results from the maximally possible interval between $t_1$ and $t_2$.

The communication unit 18 moreover comprises a mains adapter 66. The mains adapter 66 serves for a power supply. The mains adapter 66 is connected to an energy store (not shown) via a battery terminal 68 (FIGS. 2, 3).

The communication unit 44 of the glare protection device 12 is configured for receiving the signal from the transmission unit 64 as well as the bit sequence 19, 21 of the modulation unit 23 that has been modulated onto said signal. At the communication unit 44 of the glare protection unit 12, the demodulated signal of the detection device 10 is fed to a receiving buffer of a UART of the computing unit 40 of the glare protection device 12. No bit synchronization or data synchronization of the demodulator is necessary. An oversampling as well as a decoding of reception data is effected on a bit level by the integrated UART of a micro controller of the computing unit 40 of the glare protection device 12. The same bit rates must be used for the UART on the side of the communication unit 18 of the detection device 10 and on the side of the communication unit 44 of the glare protection device 12. A correlation of the reception data regarding the bit sequence 19, 21 that is to be expected is carried out in the computing unit 40 on a higher level. There are thus no requirements regarding the communication unit 44 of the glare protection device 12, nor are there requirements for the UART, regarding a bit-clock regeneration. This allows keeping the requirements to a demodulator advantageously low. FIG. 5 shows an illustrated data scanning, in particular a start bit identification, of a signal of the communication unit 18 of the detection device 10 by a communication unit 44 of the active glare protection device 12. For this the communication unit 44 of the active glare protection device 12 in particular scans each bit of the bit sequence 19, 21 sixteen times. If, for example, a scan "1" is the first zero scan, the communication unit 44 uses the scans "8", "9" and "10" to decide whether a valid start bit 69 has been received. Then a value of the further bits of the bit sequence 19, 21 is also detected via the scans "8", "9" and "10".

FIG. 6 shows a schematic flow chart of a method for an operation of the detection device 10 according to the invention. In the method, in a first method step 70 a current change occurring in the power cable 22 of the welding apparatus 16 is measured by the detection unit 14. In the first method step 70 a current change is continuously detected by the first sensor element 24, and by the signal processing unit 62. The first method step 70 realizes a rest state. The welding apparatus 16 is thus in a rest state. In the first method step 70 a status signal "welding inactive" is continuously transmitted to the glare protection device 12 by the communication unit 18. The status signal "welding inactive" is transmitted to the glare protection device 12 by sending the second bit sequence 21. For this purpose the modulation unit 23 modulates the second bit sequence 21 onto the signal of the transmission unit 64. By the continuous transmission of a status by way of the bit sequence 21, it is possible to monitor a connection between the detection device 10 and the glare protection device 12. Then follows, in a first branching 72, a monitoring whether a current change in the power cable 22 falls below a given limit value. If a current change remains below the limit value, the first method step 70 is repeated. If the detected current change exceeds the limit value, this is immediately transmitted to the communication unit 18 in a second method step 74, the communication unit 18 immediately transmitting a status signal "welding active" to the glare protection device 12. The status signal "welding active" is transmitted to the glare protection device 12 by a transmission of the first bit sequence 19. For this the modulation unit 23 modulates the first bit sequence 19 onto the signal of the transmission unit 64. Then the glare protection device 12 is immediately darkened in a third method step 76. Following this, the absolute current value in the power cable 22 is detected in a second branching 77. The detection of the absolute current value is carried out by means of the second sensor element 26. If the absolute current value exceeds a limit value, the second method step 74 is repeated and the status signal "welding active" is sent continuously to the glare protection device 12 by a transmission of the first bit sequence 19. As a result, the glare protection device 12 remains darkened. If the limit value is not exceeded, the first method step 70 is repeated. The detection unit 14 thus re-enters its rest state and the communication unit 18 sends the status signal "welding inactive" by transmitting the second bit sequence 21. The glare protection device 12 is re-opened. Following the transmission, the glare protection device 12 thus re-opens.

An opening of the glare protection device 12 is herein in particular not so time-critical and may be effected with a delay of some milliseconds. The less favorable timing behavior of the second sensor element 26 is therefore sufficient for a detection of a welding finish. As the radio transmission is always effected continuously, it is possible, besides a timely transmission of a new status, to monitor the radio connection as well.

The invention claimed is:

1. A detection device for an active glare protection device, comprising:
    a detection unit that is configured for a direct or indirect detection of at least one welding parameter of a welding apparatus; and
    at least one communication unit that is configured for a transmission of at least one information of the at least one welding parameter to the active glare protection device,
    wherein the communication unit is configured for a transmission of at least one information of the at least one welding parameter, implemented as a bit sequence of a defined length, to the active glare protection device,
    wherein the at least one communication unit is configured for a uni-directional transmission of at least one information of the at least one welding parameter to the active glare protection device,
    wherein the transmission of the at least one information of the at least one welding parameter to the active glare protection device is effected in a streaming procedure,
    wherein the detection unit is configured for a direct or indirect detection of at least two switch states of the welding apparatus, and
    wherein the at least one communication unit is configured for a direct transmission of the two switch states of the welding apparatus, implemented as mutually inverse bit sequences, to the active glare protection device.

2. The detection device according to claim 1, wherein the communication unit is configured for a wireless transmission of the at least one information of the at least one parameter to the active glare protection device.

3. The detection device according to claim 1, wherein the communication unit comprises at least one transmission unit that is configured for a direct transmission of a signal to the active glare protection device, and comprises at least one modulation unit, which is configured for a modulation of the at least one welding parameter, implemented as a bit sequence of defined length, directly onto the signal.

4. The detection device according to claim 3, wherein the at least one modulation unit is configured for a modulation of the signal of the at least one transmission unit with a modulation rate of at least 100 kbit/s.

5. The detection device according to claim 3, wherein for a direct modulation of the signal of the at least one transmission unit, the at least one modulation unit comprises at least one HF transceiver component.

6. The detection device according to claim 3, wherein the communication unit is configured for receiving a signal from the transmission unit and the bit sequence of the modulation unit that has been modulated onto the signal.

7. The detection device according to claim 3, wherein the at least one transmission unit is configured for a proprietary, non-packaged transmission of the signal to the active glare protection device.

8. The detection device according to claim 1, wherein a bit sequence of the communication unit comprises at least 4 bits.

9. The detection device according to claim 1, wherein the at least one information is always transmitted as a sequence with a same number of bits.

10. The detection device according to claim 9, wherein the bit sequence has the same number of bits independently from the at least one information contained.

11. The detection device according to claim 1, wherein one bit sequence represents each switch state, wherein the bit sequences are respectively inverse to one another such that each respective bit of the bit sequence has an opposite value.

12. The detection device according to claim 1, wherein the active glare protection device comprises a computing unit that is configured for an evaluating of the welding parameter of the welding apparatus.

13. The detection device according to claim 12, wherein the computing unit automatically darkens the glare protection filter in case of an absence of a signal from the detection device.

14. A system with an active glare protection device and with a detection device according to claim 1.

* * * * *